US012778736B2

(12) United States Patent
Shinar et al.

(10) Patent No.: US 12,778,736 B2
(45) Date of Patent: Nov. 3, 2026

(54) SYSTEMS, METHODS AND DEVICES FOR EMBOLIC PROTECTION

(71) Applicant: JAVELIN MEDICAL LTD., Yokneam (IL)

(72) Inventors: Guy Shinar, Ramat Gan (IL); Sagit Broder, Gedera (IL); Alon Baranes, Yoqneam (IL); Avi Neta, Gilon (IL); Ofer Yodfat, Modi'in (IL)

(73) Assignee: JAVELIN MEDICAL LTD., Yokneam (IL)

( * ) Notice: Subject to any disclaimer, the term of this patent is extended or adjusted under 35 U.S.C. 154(b) by 98 days.

(21) Appl. No.: 18/009,698

(22) PCT Filed: Jun. 10, 2021

(86) PCT No.: PCT/IL2021/050709
§ 371 (c)(1),
(2) Date: Dec. 9, 2022

(87) PCT Pub. No.: WO2021/250680
PCT Pub. Date: Dec. 16, 2021

(65) Prior Publication Data

US 2023/0240828 A1 Aug. 3, 2023

Related U.S. Application Data

(60) Provisional application No. 63/037,382, filed on Jun. 10, 2020.

(51) Int. Cl.
*A61F 2/01* (2006.01)
*A61B 17/34* (2006.01)

(52) U.S. Cl.
CPC .......... *A61F 2/011* (2020.05); *A61B 17/3417* (2013.01); *A61B 17/3468* (2013.01);
(Continued)

(58) Field of Classification Search
CPC ........ A61F 2/01; A61F 2/0103; A61F 2/0105; A61F 2/0108; A61F 2/011; A61F 2/014;
(Continued)

(56) References Cited

U.S. PATENT DOCUMENTS

| | | |
|---|---|---|
| 3,540,431 A | 11/1970 | Mobin-Uddin et al. |
| 4,425,908 A | 1/1984 | Simon |

(Continued)

FOREIGN PATENT DOCUMENTS

| | | |
|---|---|---|
| CN | 2601642 Y | 2/2004 |
| CN | 1911188 A | 2/2007 |

(Continued)

OTHER PUBLICATIONS

Cogo et al. "Distribution of Thrombosis in Patients with Symptomatic Deep Vein Thrombosis" Arch Intern Med/vol. 153, Dec. 27, 1993, pp. 2777-2780.

(Continued)

*Primary Examiner* — Katherine M Shi
(74) *Attorney, Agent, or Firm* — FENWICK & WEST LLP

(57) ABSTRACT

Embodiments of the present disclosure are directed to systems, methods and devices for providing, in some embodiments, embolic protection in a patient. For example, a medical device and implantation method for implanting a medical device within a blood vessel of a subject are provided and comprise, for example, providing a medical device configured for arrangement within a blood vessel, where the device comprises a filament configured to include a first device end (posterior) and a second device end (anterior), an un-deployed state including at least a portion configured to fit within a lumen of a needle, and a deployed state wherein the filament automatically forms a helix wound in a first direction as viewed from the first device end
(Continued)

to the second device end, the helix optionally including at least one of a support portion and a filter portion.

13 Claims, 4 Drawing Sheets

(52) U.S. Cl.
CPC ............ *A61F 2/0103* (2020.05); *A61F 2/012* (2020.05); *A61B 2017/3454* (2013.01); *A61F 2002/016* (2013.01); *A61F 2230/0091* (2013.01)

(58) Field of Classification Search
CPC .... A61F 2/013; A61F 2/012; A61F 2002/015; A61F 2002/016; A61F 2/88; A61F 2/885; A61F 2230/0091; A61F 2220/0016; A61F 2220/0008; A61F 2002/068; A61F 2230/0067
See application file for complete search history.

(56) References Cited

U.S. PATENT DOCUMENTS 4,494,531 A 1/1985 Gianturco
4,722,350 A 2/1988 Armeniades et al.
5,059,205 A 10/1991 El-Nounou et al.
5,350,397 A 9/1994 Palermo et al.
5,413,586 A 5/1995 Dibie et al.
5,634,942 A 6/1997 Chevillon et al.
5,649,949 A 7/1997 Wallace et al.
5,669,931 A 9/1997 Kupiecki
5,695,507 A 12/1997 Auth et al.
5,733,329 A 3/1998 Wallace et al.
5,800,454 A 9/1998 Jacobsen et al.
5,868,754 A 2/1999 Levine et al.
5,895,398 A 4/1999 Wensel
5,957,940 A 9/1999 Tanner et al.
5,976,172 A 11/1999 Homsma et al.
6,007,558 A 12/1999 Ravenscroft et al.
6,059,825 A 5/2000 Hobbs et al.
6,066,158 A 5/2000 Engelson et al.
6,074,341 A 6/2000 Anderson et al.
6,093,199 A 7/2000 Brown et al.
6,099,549 A 8/2000 Bosma et al.
6,123,715 A 9/2000 Amplatz
6,152,144 A 11/2000 Lesh et al.
6,214,025 B1 4/2001 Thistle et al.
6,238,403 B1 5/2001 Greene, Jr. et al.
6,344,052 B1 2/2002 Greenan et al.
6,368,346 B1 4/2002 Jadhav
6,375,671 B1 4/2002 Kobayashi et al.
6,395,017 B1 5/2002 Dwyer et al.
6,652,558 B2 11/2003 Patel et al.
6,669,707 B1 12/2003 Swanstrom et al.
6,673,089 B1 1/2004 Yassour et al.
6,730,108 B2 5/2004 Van et al.
6,953,471 B1 10/2005 Lilly et al.
7,128,073 B1 10/2006 Van et al.
7,144,363 B2 12/2006 Pai et al.
7,261,731 B2 8/2007 Patel et al.
7,306,624 B2 12/2007 Yodfat et al.
7,572,273 B2 8/2009 Mazzocchi et al.
7,704,267 B2 4/2010 Tessmer
7,716,801 B2 5/2010 Douk et al.
7,740,644 B2 6/2010 Beulke et al.
7,794,494 B2 9/2010 Sahatjian et al.
7,955,344 B2 6/2011 Finitsis
8,057,507 B2 11/2011 Horan et al.
8,092,487 B2 1/2012 Streeter et al.
8,118,858 B2 2/2012 Tseng et al.
8,137,396 B2 3/2012 Busold et al.
8,206,412 B2 6/2012 Galdonik et al.
8,221,446 B2 7/2012 Pal et al.
8,236,009 B2 8/2012 Saadat et al.
8,252,018 B2 8/2012 Valaie
9,220,588 B2 12/2015 Shinar et al.
9,592,110 B1 3/2017 Dan et al.
10,028,819 B2 7/2018 Shinar et al.
10,226,321 B2 3/2019 Shinar et al.
10,507,023 B2 12/2019 Poulsen
10,531,943 B1 1/2020 Dan et al.
10,925,708 B2 2/2021 Shinar et al.
11,202,699 B2 12/2021 Yair et al.
11,207,170 B2 12/2021 Shinar et al.
11,484,397 B2 11/2022 Dan et al.
2001/0007946 A1 7/2001 Lenker et al.
2001/0031980 A1 10/2001 Wensel et al.
2002/0010481 A1 1/2002 Jayaraman
2002/0188170 A1 12/2002 Santamore et al.
2003/0100939 A1 5/2003 Yodfat et al.
2003/0212428 A1 11/2003 Richter
2004/0082962 A1 4/2004 Demarais et al.
2005/0004575 A1 1/2005 Sgro et al.
2005/0177181 A1 8/2005 Kagan et al.
2006/0167489 A1 7/2006 Satake et al.
2006/0212047 A1 9/2006 Abbott et al.
2007/0010857 A1 1/2007 Sugimoto et al.
2007/0066863 A1 3/2007 Rafiee et al.
2007/0156123 A1 7/2007 Moll et al.
2007/0239199 A1 10/2007 Swaminathan
2008/0108933 A1 5/2008 Yu et al.
2008/0147111 A1 6/2008 Johnson et al.
2008/0183206 A1 7/2008 Batiste
2008/0221600 A1 9/2008 Dieck et al.
2008/0269789 A1 10/2008 Eli
2009/0054905 A1 2/2009 Levy
2009/0054912 A1 2/2009 Heanue et al.
2009/0099591 A1 4/2009 Nardone et al.
2009/0138066 A1 5/2009 Leopold et al.
2009/0163926 A1 6/2009 Sos
2009/0187211 A1 7/2009 Mackiewicz
2009/0228020 A1 9/2009 Wallace et al.
2010/0016881 A1 1/2010 Fleck et al.
2010/0023024 A1 1/2010 Zeiner et al.
2010/0234852 A1 9/2010 Shinohara et al.
2010/0268204 A1 10/2010 Tieu et al.
2010/0280522 A1 11/2010 Barry et al.
2011/0021984 A1 1/2011 Kirschenman et al.
2011/0022149 A1 1/2011 Cox et al.
2011/0137394 A1 6/2011 Lunsford et al.
2011/0226379 A2 9/2011 Johnson
2012/0165919 A1 6/2012 Cox et al.
2012/0172921 A1 7/2012 Yamanaka et al.
2012/0197379 A1 8/2012 Laske et al.
2012/0245614 A1 9/2012 Drasler
2012/0289988 A1 11/2012 Riina et al.
2012/0316597 A1 12/2012 Fitz et al.
2013/0184658 A1 7/2013 Duncan
2014/0004503 A1 1/2014 Cima et al.
2014/0114337 A1 4/2014 Fung et al.
2014/0135799 A1 5/2014 Henderson
2014/0277097 A1 9/2014 Castleberry et al.
2015/0196301 A1 7/2015 Bodewadt et al.
2015/0297241 A1 10/2015 Yodfat et al.
2016/0220371 A1 8/2016 Keane
2017/0367808 A1 12/2017 Shinar et al.
2018/0103960 A1 4/2018 Poulsen
2019/0021836 A1* 1/2019 Yair ........................ A61F 2/013
2019/0269413 A1 9/2019 Yodfat et al.
2021/0169631 A1 6/2021 Shinar et al.
2022/0104931 A1 4/2022 Shinar et al.
2022/0110736 A1 4/2022 Yair et al.
2024/0350249 A1 10/2024 Shinar et al.

FOREIGN PATENT DOCUMENTS

CN 201768049 U 3/2011
CN 103313751 A 9/2013
DE 102005010222 A1 9/2006
EP 0121447 A1 10/1984
EP 0865772 A1 9/1998
JP H07000405 A 1/1995

(56) References Cited

FOREIGN PATENT DOCUMENTS

| | | | |
|---|---|---|---|
| WO | WO-9104716 | A1 | 4/1991 |
| WO | WO 1991/007928 | A1 | 6/1991 |
| WO | WO-9823322 | A1 | 6/1998 |
| WO | WO-9834546 | A1 | 8/1998 |
| WO | WO-2004098420 | A2 | 11/2004 |
| WO | WO-2005051235 | A1 | 6/2005 |
| WO | WO-2005117750 | A1 | 12/2005 |
| WO | WO-2006055443 | A2 | 5/2006 |
| WO | WO-2006084156 | A2 | 8/2006 |
| WO | WO-2007005996 | A2 | 1/2007 |
| WO | WO-2008042266 | A2 | 4/2008 |
| WO | WO-2008127328 | A1 | 10/2008 |
| WO | WO-2009125744 | A1 | 10/2009 |
| WO | WO-2010127083 | A2 | 11/2010 |
| WO | WO-2010134914 | A1 | 11/2010 |
| WO | WO-2011014703 | A1 | 2/2011 |
| WO | WO-2012094251 | A2 | 7/2012 |
| WO | WO-2013179137 | A2 | 12/2013 |
| WO | WO-2014102767 | A2 | 7/2014 |
| WO | WO-2014111911 | A1 | 7/2014 |
| WO | WO-2016110848 | A1 | 7/2016 |
| WO | WO-2018073830 | A2 | 4/2018 |
| WO | WO-2021250680 | A1 | 12/2021 |

OTHER PUBLICATIONS

Cousin et al. "Incidence et distribution des thromboses veineusesdes des membres inférieurs diagnostiquées par écho-doppler au décours de prothèses de hanche, de genou et de fractures de hanche. Résultats portant sur 5981 explorations et 2123 thromboses en dix ans" Journal des Maladies Vasculaires (2011) 36(4), 243-253 (English summary).

Decousus et al. "A Clinical Trial of Vena Caval Filters in the Prevention of Pulmonary Embolism in Patients with Proximal Deep-Vein Thrombosis", The New England Journal of Medicine, Feb. 12, 1998, 338, pp. 409-415.

International Preliminary Report on Patentability, mailed Dec. 2, 2014, for International Application No. PCT/IB2013/001336 (6 total pages).

International Preliminary Report on Patentability, mailed Dec. 22, 2022, for International Application No. PCT/IL2021/050709 (11 total pages).

International Preliminary Report on Patentability, mailed Jul. 20, 2017, for International Application No. PCT/IL2016/050016 (10 total pages).

International Preliminary Report on Patentability, mailed Jul. 30, 2015, for International Application No. PCT/IL2013/050981 (15 total pages).

International Preliminary Report on Patentability, mailed Jul. 9, 2015, for International Application No. PCT/IL2013/050979 (10 total pages).

International Preliminary Report on Patentability, mailed May 2, 2019, for International Application No. PCT/IL2017/051157 (9 total pages).

International Search Report and Written Opinion for Application No. PCT/IL2021/050709, mailed Oct. 6, 2021 (13 total pages).

International Search Report and Written Opinion for International Application No. PCT/IB2013/001336 mailed Jan. 24, 2014 (8 total pages).

International Search Report and Written Opinion, mailed Jun. 23, 2014, for International Application No. PCT/IL2013/050979 (13 total pages).

International Search Report for International Application No. PCT/IL13/50981 mailed Jun. 23, 2014 (5 total pages).

International Search Report for International Application No. PCT/IL2016/050016 mailed Jun. 9, 2016 (2 total pages).

International Search Report for International Application No. PCT/IL2017/051157, mailed May 7, 2018 (4 total pages).

Ouriel et al. "The anatomy of deep venous thrombosis of the lower extremity" Journal of Vascular Surgery, May 2000, 31, pp. 895-900.

Thors et al. "Resorbable Inferior Vena Cava Filters: Trial in an In-vivo Porcine Model" J Vasc Interv Radiol 2011, vol. 22, No. 3, Mar. 2011, 330-335.

* cited by examiner

SYSTEMS, METHODS AND DEVICES FOR EMBOLIC PROTECTION

RELATED APPLICATIONS

This application is a national stage entry of International Application No. PCT/IL2021/050709, filed Jun. 10, 2021, entitled, "Systems, Methods and Devices for Embolic Protection", which claims benefit of and priority to U.S. provisional patent application No. 63/037,382, filed Jun. 10, 2020, entitled, "Systems, Methods and Devices for Embolic Protection", the entire disclosure of which is herein incorporated by reference in its entirety.

FIELD OF THE DISCLOSURE

The field of the present disclosure is embolic protection devices. More specifically, the field of the present disclosure is embolic protection for the prevention of brain stoke and/or pulmonary embolism.

BACKGROUND

An embolism is an event of the lodging of an embolus (a detached intravascular mass) into a narrow vessel, which causes a blockage in a part of the body. An embolism can be classified as to whether it enters the circulation in arteries or veins. Arterial embolism can start in the heart or in large arteries, and can cause occlusion and/or infarction in any part of the body. Embolus lodging in the brain from either the heart, the aorta, or the carotid arteries can cause an ischemic stroke. Venous embolisms, which form in systemic veins, can lodge in the lungs after passing through the right side of the heart. This deleterious condition is known as pulmonary embolism.

Distal embolization can occur spontaneously (in particular, in the setting of atrial fibrillation) or be induced by manipulation of the heart, large arteries, or veins, either in the setting of open surgery, or in the setting of endovascular manipulation such as balloon angioplasty, stenting, or transcatheter valve replacement. Distal embolizations can be prevented by pharmacological treatment (anti-coagulants). While effective, anticoagulants have the deleterious side effect of high bleeding risk, which may be severe or even life-threatening. In addition, many patients do not tolerate well anticoagulant medication and cannot enjoy the embolic protection that it may render.

Distal embolization may also be prevented or by using mechanical filtering devices (distal embolic protection devices), which are placed between the embolic source and the distal vasculature, However, many prior and current devices fail to adequately address the problem, and in fact, in many circumstances, cause problems (e.g., become occluded, migrate from the implantation site, and the like).

In some patients, distal embolization may be prevented by a combined approach, including both mechanical filtering devices concomitantly with anti-coagulants. This approach might be desirable in atrial fibrillation patients that had a recent stroke, who need extra protection against a recurrent embolic stroke event.

SUMMARY

Accordingly, embodiments of the present disclosure may be used to address embolism events in blood vessels of the body.

In some embodiments, a medical device configured for arrangement within a blood vessel is provided and comprises a filament configured to include a first device end (posterior) and a second device end (anterior), an un-deployed state including at least a portion (and in some embodiments, substantially all or all of the filament) configured to fit within a lumen of a needle, and a deployed state wherein the filament automatically forms a helix wound in a first direction as viewed from the first device end to the second device end. In some embodiments, the helix may include a support portion and a filter portion. The device can be configured for deploying within a blood vessel of a subject in an implantation direction, such that the first device end points towards a subject first end, and the second device end points towards a subject second end. The first direction of the filament corresponds to one of a clockwise or a counterclockwise direction upon the device being deployed in a blood vessel arranged on a first side of the body of the subject. The first direction of the filament corresponds to the other of the clockwise or counterclockwise direction upon the device being deployed in a blood vessel on a second side of the body of the subject.

In some embodiments, a medical device implantation method for implanting a medical device (like those above) within a blood vessel of a subject is described. The method includes, providing a medical device configured for arrangement within a blood vessel, the device comprising a filament configured to include a first device end (posterior) and a second device end (anterior), an un-deployed state including at least a portion (and in some embodiments, substantially all or all of the filament) configured to fit within a lumen of a needle, and a deployed state wherein the filament automatically forms a helix wound in a first direction as viewed from the first device end to the second device end (as noted above, the helix optionally includes, in some embodiments, at least one of a support portion, and a filter portion. The method also includes deploying the device within a blood vessel of a subject in an implantation direction, such that the first device end points towards a subject first end, and the second device end points towards a subject second end. The first direction of the filament corresponds to one of a clockwise or a counterclockwise direction upon the device being deployed in a blood vessel arranged on a first side of the body of the subject, and the first direction of the filament corresponds to the other of the clockwise or counterclockwise direction upon the device being deployed in a blood vessel on a second side of the body of the subject.

The above noted embodiments (as well as other embodiments, see, e.g., below embodiments in summary and detailed description) may include one and/or another of (in some embodiments, a plurality of, and in some embodiments, a majority of, and in some embodiments, all of) the following additional structures, steps, functionality, and/or clarifications, yielding yet further embodiments of the present disclosure:

- the first side comprises the left side of the body of the subject, and the second side comprises the right side of the body of the subject;
- the blood vessel on the left side of the body comprises the left carotid artery, and the blood vessel on the right side of the body comprises a right carotid artery;
- the distal end of the needle includes and opening and a bevel along a bevel plane;
- the bevel plane is arranged during implantation such that it faces the midline of the subject;
- the bevel plane is arranged during implantation such that it faces the lateral direction of the subject;

the bevel plane is arranged during implantation such that it faces the caudal direction of the subject;

the bevel plane is arranged during implantation such that it faces the cranial direction of the subject;

the bevel plane is arranged during implantation such that it faces the midline of the subject and faces the caudal direction of the subject;

the bevel plane is arranged during implantation such that it faces the midline of the subject and faces the cranial direction of the subject;

the bevel plane is arranged during implantation such that it faces the lateral direction of the subject and faces the caudal direction of the subject; and the bevel plane is arranged during implantation such that if faces the lateral direction of the subject and faces the cranial direction of the subject.

In some embodiments, an embolic protection device (EPD) configured for arrangement within a blood vessel is provided and comprises a first device end (posterior) and a second device end (anterior), an un-deployed state including at least a portion thereof (and in some embodiments, substantially all or all thereof) configured to fit within a lumen of a needle, and a deployed state where the filament automatically forms a helix wound in a first direction as viewed from the first device end to the second device end, the helix optionally including at least one of a support portion and a filter portion. The EPD is deployed within each carotid artery such that the first end points in the cranial direction of the subject, the distal end of the needle includes and opening and a bevel along a bevel plane, the bevel plane is arranged during implantation such that it faces both the midline and the caudal direction of the subject, the first direction of the filament corresponds to a clockwise direction upon the device being deployed in the right carotid artery, and the first direction of the filament corresponds to a counterclockwise direction upon the device being deployed in the left carotid artery.

In some such embodiments, an embolic protection device system is provided, which in addition to the above noted implantation device (e.g., EPD device or other filament based medical device), a needle or catheter is also included/provided and configured to house an EPD/medical device prior to implantation and to implant the EPD/medical device.

In some embodiments, a method for implanting an embolic protection device (EPD) is provided, where the EPD comprises a first end (posterior) and a second end (anterior), an un-deployed state including at least a portion thereof (and in some embodiments, substantially all or all thereof) configured to fit within a lumen of a needle, and a deployed state wherein the filament automatically forms a helix wound in a first direction as viewed from the first end to the second end, the helix optionally including at least one of a support portion and a filter portion. The EPD is deployed within each carotid artery such that the first end points in the cranial direction of the subject, and the distal end of the needle includes and opening and a bevel along a bevel plane. The bevel plane is arranged during implantation such that it faces both the midline and the caudal direction of the subject, the first direction of the filament corresponds to a clockwise direction upon the EPD being deployed in the right carotid artery, and the first direction of the filament corresponds to a counterclockwise direction upon the EPD being deployed in the left carotid artery.

These and other embodiments, as well other objects and advantages of inventions disclosed herein will be even more evident by reference to the following detailed description and figures, a brief description of which follows.

DETAILED DESCRIPTION OF SOME EMBODIMENTS

Embodiments of the present disclosure are related those disclosed in PCT publication nos. WO2018/073830, with an international filing date of 20 Oct. 2017, WO2013/179137, with an international filing date of 30 May 2013, and WO/2014/111911, with an international filing date of 27 Nov. 2013, each of which, in its entirety, is herein incorporated by reference. These aforementioned publications hereinafter referred to as "Prior Disclosures".

Figure 1A:
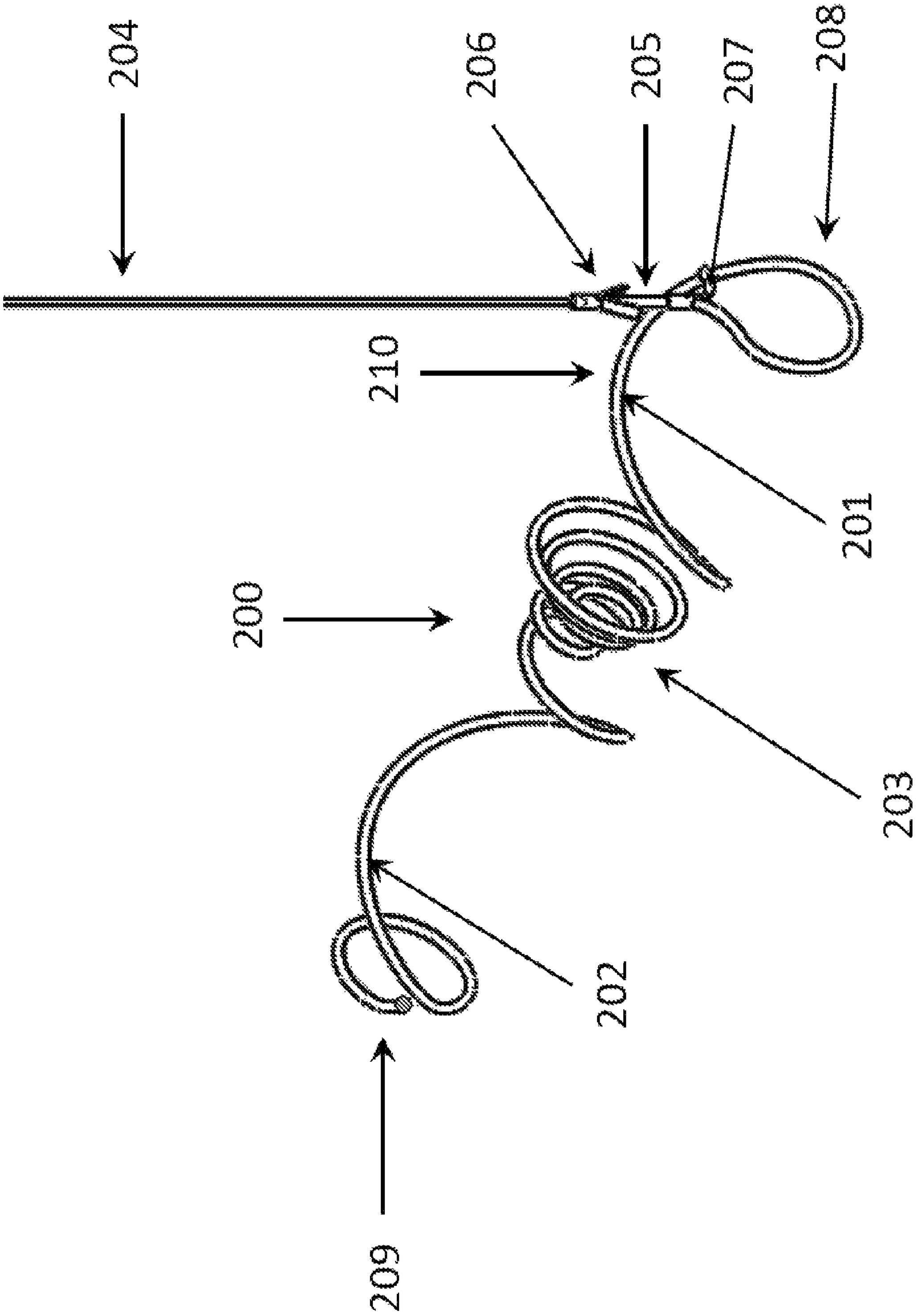
FIG. 1A illustrates a deployed state of an embolic protection device having a first and a second supporting portion with a filter portion interposed therebetween, in which the filament is wound in a counterclockwise direction, according to some embodiments of the present disclosure.
Figure 1B:
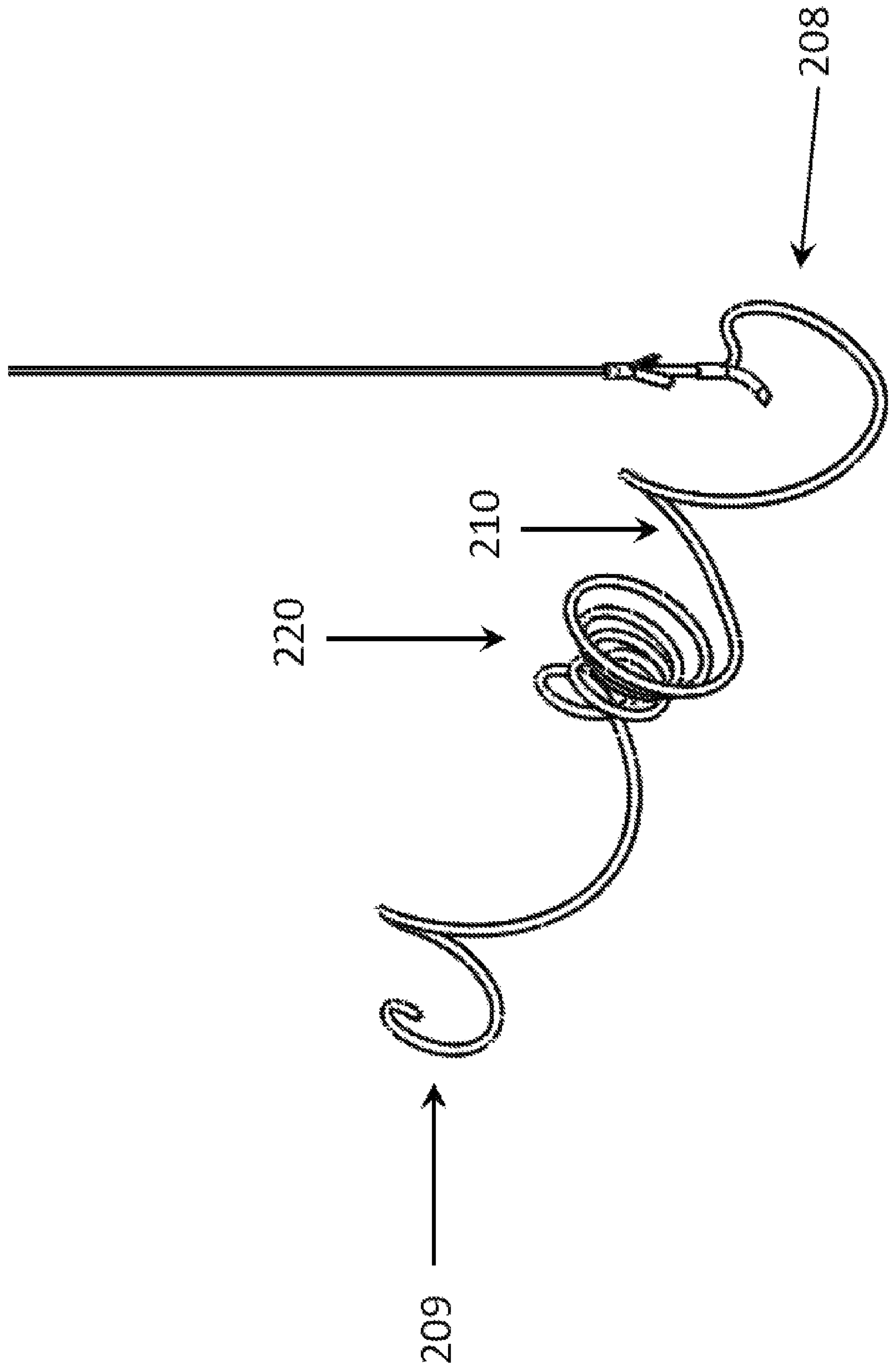
FIG. 1B illustrates a deployed state of an embolic protection device having a first and a second supporting portion with a filter portion interposed therebetween, in which the filament is wound in a clockwise direction, according to some embodiments of the present disclosure.

FIGS. 1A-1B illustrate a deployed state of embolic protection devices (which may be referred to as EPDs, or an EPD in the singular), according to some embodiments of the present disclosure. As shown in FIG. 1A, EPD 200 includes a filament 210 including a first supporting portion 201 and a second supporting portion 202, and a filtering portion 203 interposed between the first and the second supporting portions 201 and 202. EPD 200, in some embodiments, may also include at least one of, and in some embodiments, a plurality of, and in some embodiments, all of: a pulling wire 204, a stem 205, an anchor 206, and a stopper 207. When viewed from end 208 (which may be referred to as the rear or posterior end of EPD 200) to end 209 (which may be referred to as the front or anterior end of EPD 200), and also when viewed from the front end 209 to the rear end 208, filament 210 is wound in the counterclockwise direction.

Figure 3:
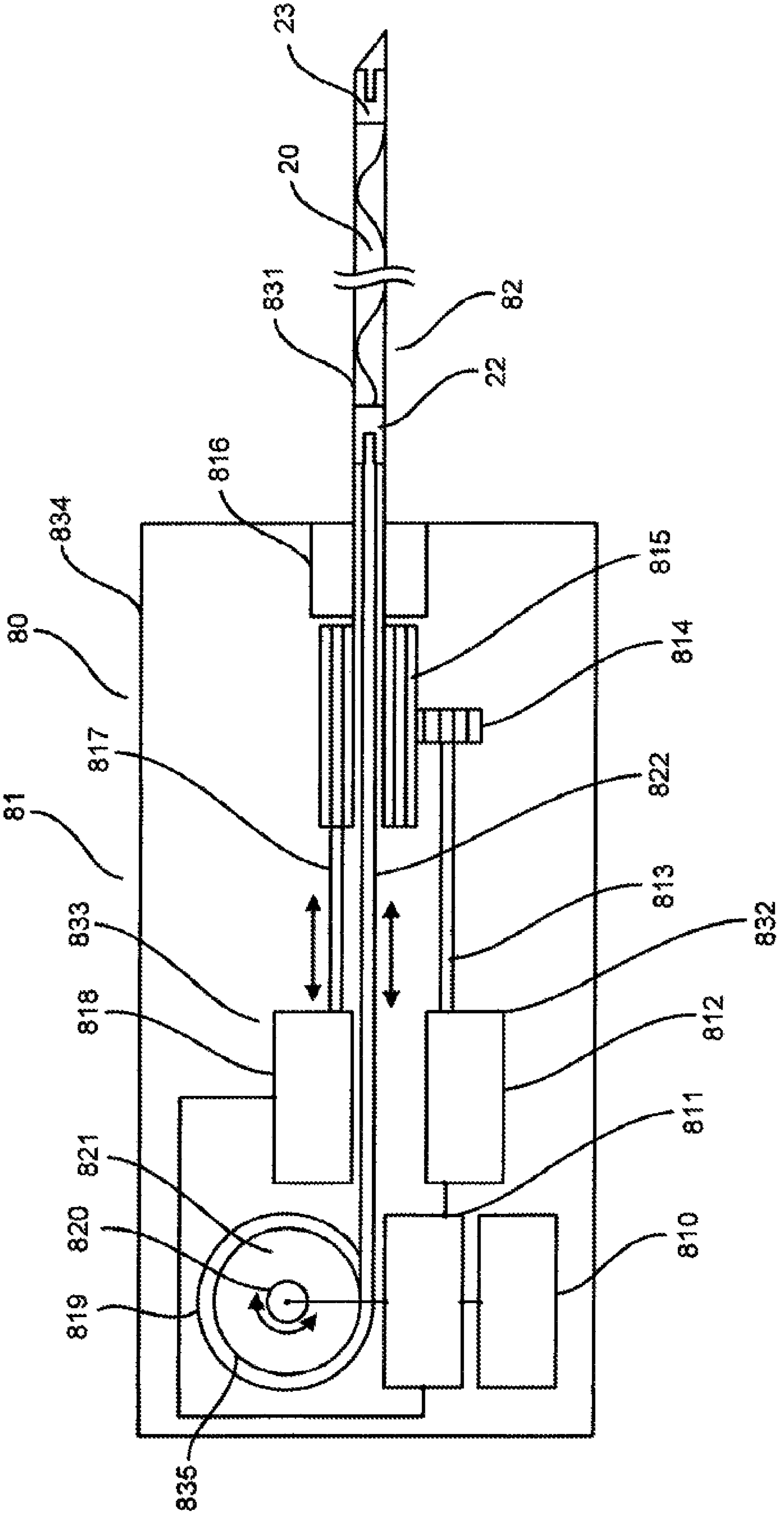
FIG. 3 is a schematic representation of a system (which may be automated) configured for implanting an embolic protection device according to some embodiments of the present disclosure.

In some embodiments, EPD 200 may include an undeployed, substantially linear state (which includes a substantially straight filament, according to some embodiments) configured to fit within the lumen of a cannula, catheter or needle (collectively herein may be referred to as a needle, see, e.g., ref. no. 831, FIG. 3). The filament, stem, first supporting portion, filtering portion, anchor, stopper, pulling wire (and, in some embodiments, an undeployed state) may be similar to those described in the Prior Disclosures. Moreover, EPD 200 may be implanted in a vessel, such as an artery or a vein, using any of the embolic protection implantation systems and/or deployment/implantation methods described in the Prior Disclosures.

In some embodiments, the diameter of the second supporting portion is between 0.1 and 2 mm less than the diameter of the first supporting portion, which has been found to improve the implantation success rate as compared to a device where both supporting portions are of the same diameter. Moreover, in some embodiments, the second supporting portion may, or may not (according to some embodiments), be oversized compared to the vessel diameter to which the EPD is implanted. In some embodiments, oversizing the first supporting portion with respect to a carotid diameter by 0.2-0.7 mm, while having the second supporting portion undersized by 0.5 mm compared to the first supporting portion, enables both high implantation success rate and good post-implantation device stability.

The second supporting portion may otherwise be substantially similar to the first supporting portion (according to some embodiments).

As shown in FIG. 1B, an EPD 220 according to some embodiments of the present disclosure is described. In some embodiments, EPD 220 is substantially similar to EPD 200, except that EPD 220 is wound in a clockwise rather than counterclockwise direction when viewed either from end 208 to end 209, or from end 209 to end 208.

In some embodiments, upon deploying EPDs (according to some embodiments) in carotid arteries (e.g., to provide protection against stroke), it may be advantageous to deploy the EPDs in the caudal (i.e., head to feet) direction ("rear" end 208 pointing towards the head, and "front" end 209 pointing towards the feet). In such deployments, and in some embodiments, it is advantageous to:

- deploy an EPD with a deployed state in which the filament is wound counterclockwise, such as EPD 200, in the left carotid artery; and/or
- deploy an EPD having a deployed state in which the filament is wound in the clockwise direction, such as EPD 220, in the right artery.

Example

- 46 units of EPD 220 (wound in a clockwise direction) and 127 units of EPD 200 (wound in a counterclockwise direction) were deployed caudally under ultrasound guidance in the right carotid arteries of sheep. The implantation success rate was 96% (44/46) for EPD 220, and 73% (93/127) for EPD 200.
- 83 units of EPD 200 were deployed caudally under ultrasound guidance in the left carotid arteries of sheep. The implantation success rate was 100% (83/83).

These data sets, according to certain embodiments, demonstrate that caudal deployment of EPD 200 (wound in a counterclockwise direction) in the left carotid, and EPD 220 (wound in a clockwise direction) in the right carotid, optimize the success rate of implantation in the caudal direction. This is a counterintuitive finding as the right and left carotids are similar tubular structures and therefore, at first glance, it should not matter whether the EPDs are wound in the counterclockwise or the clockwise direction. However, the symmetry between right and left is broken because of the presence of anatomical structures such as the trachea, which might affect the compliance of the right and left arterial walls in different ways.

In some embodiments, when deploying EPDs (according to some embodiments) in carotid arteries (e.g., to provide protection against stroke), it is advantageous to deploy implants in the cranial (feet to head) direction ("rear" end 208 pointing towards the feet and "front" end 209 pointing towards the head). Accordingly, in such embodiments it is advantageous to:

- deploy an EPD having a deployed state in which the filament is wound counterclockwise, such as EPD 200, in the right carotid artery; and/or
- to deploy an EPD having a deployed state in which the filament is wound in the clockwise direction, such as device 220, in the left artery.

Figure 2:
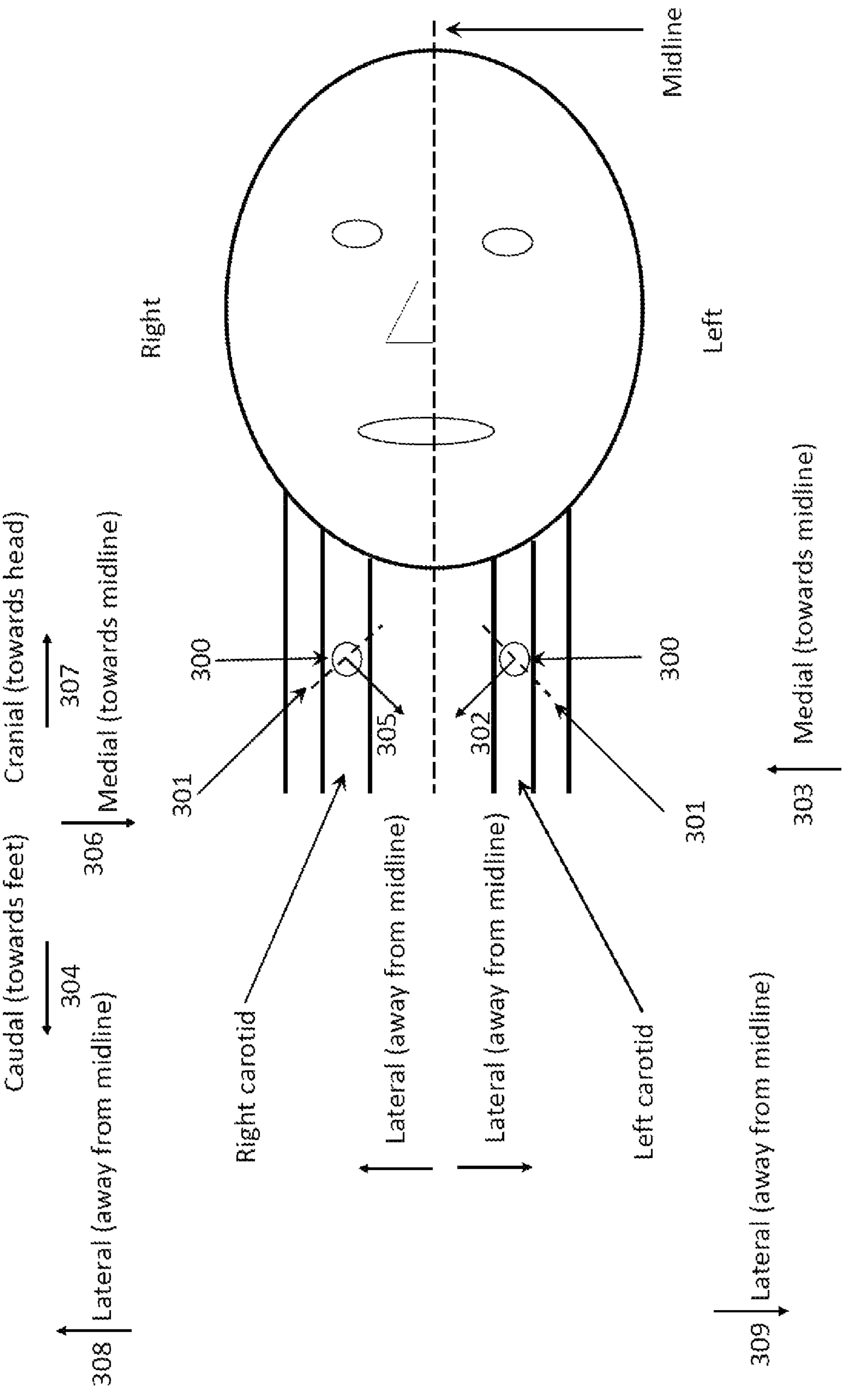
FIG. 2 is a schematic illustration of a head and neck of a human patient lying on the back and viewed from above, and orientations/positions, according to some embodiments, for a bevel of a needle or cannula, for implanting an embolic protection device implanting in a body vessel.

FIG. 2 illustrates a top view of a human patient lying on his/her back, and orientation/positioning, according to some embodiments, for the bevel of a needle or cannula (see also, e.g., ref. no. 831, FIG. 3), used in methods and systems disclosed herein, for implanting in a body vessel an embolic protection device. Accordingly, needle/cannula 300 is shown (top view showing needle transverse cross section) including bevel 301, where a dotted line indicates a line connecting the midpoints of the bevel walls at the two sides of the bevel, and an arrow indicates the direction towards which the opening of the needle bevel is pointing, may be included in any of the embolic protection implantation systems and associated embolic protection device implantation methods described in the Prior Disclosures.

In some embodiments, where EPDs (according to some embodiments) are deployed in carotid arteries (e.g., to provide protection against stroke), it is advantageous to deploy an EPD having a deployed state in which the filament is wound counterclockwise, such as EPD 200, in the left carotid artery, and in the caudal direction. In such cases/embodiments, orientation 302 of bevel 301 is approximately midway between the medial direction 303 and the caudal direction 304.

In some embodiments, where EPDs (according to some embodiments) are deployed in carotid arteries (e.g., to provide protection against stroke), it is advantageous to deploy an EPD having a deployed state in which the filament is wound clockwise, such as EPD 220, in the right carotid artery, and in the caudal direction. In such a case, orientation 305 of bevel 301 may be about midway between the medial direction 306 and the caudal direction 304.

In some embodiments, where EPDs (according to some embodiments) are deployed in carotid arteries (e.g., to provide protection against stroke), it is advantageous to deploy an EPD having a deployed state in which the filament is wound counterclockwise, such as device 200, in the right carotid artery, and in the cranial direction. In such cases/embodiments, the orientation of the bevel may be about midway between the medial direction 303 and the cranial direction 307.

In some embodiments, where EPDs (according to some embodiments) are deployed in carotid arteries (e.g., to provide protection against stroke), it is advantageous to deploy an EPD having a deployed state in which the filament is wound clockwise, such as EPD 220, in the left carotid artery, and in the cranial direction. In this case, the orientation of the bevel may be about midway between the medial direction 306 and the cranial direction 307.

In some embodiments, where EPDs are deployed in the caudal direction, it is advantageous for the bevel orientation of the delivery needle to be in the caudal direction irrespective of whether the embolic protection device is wound counterclockwise or clockwise. Upon an EPD being deployed in the cranial direction, in some embodiments, it is advantageous for the bevel orientation to be in the cranial direction irrespective of whether the embolic protection device is wound counterclockwise or clockwise.

In some embodiments, where EPDs are deployed in the caudal direction, and the EPD has a counterclockwise winding, it is advantageous for the bevel orientation of the delivery needle to be arranged be midway between the caudal and medial direction 303 if implantation is made in the left artery, and midway between the caudal and lateral direction 308 if the implantation is made in the right artery In some embodiments, in a setting where implantation is made in the caudal direction, and the EPD has a clockwise winding, it is advantageous for the bevel orientation of the delivery needle to be midway between the caudal and medial direction 306 if implantation is made in the right artery, and midway between the caudal and lateral direction 309 if the implantation is made in the left artery.

An EPD according to disclosed embodiments, can be implanted (generally), and as set out above, via the system disclosed in FIG. 3 (which corresponds to one of the system's disclosed in WO2014/111911, incorporated herein by reference, see, e.g., FIG. 8 and corresponding description), a brief description of which follows. System 80 comprises a patient-external unit 81 and a patient-internal unit 82. Patient external unit 81 may be disposable or reusable. Patient-internal unit 82 may be disposable. Device 80 may be sterilizable using means known in the art. Patient-internal unit 82 may reversibly connect and disconnect from patient-external unit 81 whenever unit 81 is reusable. Such reversible connection means may comprise any known reversible connections means such as, for example, a screw, a magnet or a snap.

Patient-external unit 81 may comprise a power supply 810, a control unit 811, driving mechanisms 819, 832, and 833, gear ring 815, and bearing 816, all of which may be housed in housing 834. Patient-internal unit 82 may comprise needle 831 and embolic protection device 20. Embolic protection device 20 may reside in its undeployed, substantially linear state within the lumen of needle 831.

Driving mechanism 833 may configured to advance or retract needle 831 with respect to housing 834. Driving mechanism 832 is configured to rotate needle 831. Driving mechanism 819 can be configured to advance or retract device 20 with respect to housing 834. Bearing 816 is configured to allow needle 831 to rotate with respect to housing 834. Gear ring 815 may be configured to couple needle 831 to driving mechanisms 832 and 833. Gear ring 815 may attach to the proximal end of needle 831 around the circumference of needle 831.

Driving mechanism 833 may comprise a motor 818 and a shaft 817. Shaft 817 may be configured to transmit the linear (advancement/retraction) motion generated by motor 818 to gear ring 815, thereby advancing or retracting gear wheel 815 (and needle 831 to which gear wheel 815 may be rigidly connected) with respect to housing 834. Gear wheel 815 may be connected to shaft 817 in the following way: gear wheel 815 may comprise a circular groove (not shown) at its proximal end, and the tip of shaft 817 may be inserted in this groove. The shape of the groove may be made such that its opening to the proximal face of gear wheel 815 may be narrower than its interior. Similarly shaft 817 may comprise a bulb at its distal tip, whose maximal width is larger than the size of the opening of the groove. Thus, whenever the tip of shaft 817 is inserted in the groove, linear motion of shaft 817 is translated to likewise linear motion of gear wheel 815 (and needle 831) by the coupling between the shaft and the groove. However, gear wheel 815 is free to rotate without hindrance from shaft 817 because the tip of shaft 817 is free to slide within the channel of the groove.

Driving mechanism 832 may comprise a motor 812, a shaft 813, and a gear wheel 814. Shaft 832 is configured to transmit the rotary motion generated by motor 812 to gear wheel 814.

Gear ring 815 and gear wheel 814 may be connected by means of interlocking gear teeth. Therefore, the rotation of gear wheel 814 is translated to rotation of gear ring 815. Because gear ring 815 is rigidly connected to needle 831, rotation of gear wheel 814 translates to rotation of needle 831. Gear wheel 814 may be configured to slide with respect to gear ring 815 in the linear (advancement/retraction) direction. In this way, rotational coupling between gear wheel 814 and gear ring 815 is preserved regardless of the linear position of bear ring 815 (and needle 831). Needle 831 may be free to rotate with respect to housing 834 by means of bearing 816.

Driving mechanism 819 may comprise a motor 835 and a push wire 822. Motor 835, may comprise a stator 820 and a rotor 821. The proximal portion of flexible push wire 822 may be rolled around rotor 821. The distal end of push wire 822, which may reside in the lumen of needle 831, may be coupled to the proximal end of device 20. The coupling may be reversible. For example, disconnection of the coupling may be realized using mechanical or electrical means as known in the art, such as, electrolysis.

Whenever motor 835 is configured to cause rotor 821 to rotate in the counterclockwise direction, push wire 822 may then advance relative to needle 831, and device 20 caused to advance relative to the needle. Whenever motor 835 is made to cause rotor 821 to rotate in the clockwise direction, push wire 822 is retracted with respect to needle 831. This may or may not cause device 20 to also retract with respect to the needle, depending on the type of coupling between push wire 822 and the proximal part of device 20.

Whenever needle 831 rotates with respect to housing 834, the rotational motion is transmitted to device 20. The transmission of rotational motion between the needle and the device may be realized by friction between the interior walls of the needle and the device.

In operation, power supply 810 provides electrical or mechanical power to control unit 811. Control unit 811 transmits power and/or signals to driving mechanisms 832, 833, and 81 according to a predetermined program stored in the control unit (for example), or by instructions from the operator that are transmitted to the control unit via its man machine interface. Any combination of linear and/or rotational motions of needle 831 and/or device 20 with respect to external housing 834 may be implemented.

In some embodiments, the implantation of embolic filtering device 20 by means of automatic system 80 in a body vessel may proceed as follows. First, a physician determines that it is desirable to implant filtering embolic device 20 in the body vessel. Under the guidance of a suitable imaging modality (not shown), such as, for example, ultrasound, high resolution ultrasound, or CT scanning, or without imaging guidance at all, the operator punctures the skin adjacent to the vessel using the sharp end of needle 831. The operator then carefully advances system 80 through the subcutaneous tissue, and transversely punctures the vessel. Once this positioning is achieved, the operator instructs control unit 811 to execute a predetermined program (which optionally depends on inputs from one or more sensor), which causes device 20 to be properly exteriorized, and the embolic protection device 20 is properly arranged within the lumen. Once the device 20 is properly exteriorized, the operator extracts system 80 from the patient's body.

Other Considerations

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all structure, parameters, dimensions, materials, functionality, steps and configurations described herein are meant to be an example and that the actual structure, parameters, dimensions, materials, functionality, steps and configurations will depend upon the specific application or applications for which the inventive teachings is/are used. Those skilled in the art will recognize, or be able to ascertain using no more than routine experimentation, many equivalents to the specific inventive embodiments described herein (and recited elements thereof). It is, therefore, to be understood that the foregoing embodiments are presented by way of example only and that, within the scope of the claims supported by the present disclosure, and equivalents thereto, inventive embodiments may be practiced otherwise than as specifically described and claimed. Inventive embodiments of the present disclosure are also directed to each individual feature, system, article, structure, material, kit, functionality, step, clarification and method described herein. In addition, any combination of two or more such features, systems, articles, structure, materials, kits, functionalities, steps, clarifications and methods, if such are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, as noted, various inventive concepts may be embodied as one or more methods. Accordingly, the acts performed as part of the method may be ordered in any suitable way, and may be constructed in which acts are performed in an order different than disclosed, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The terms "can" and "may" are used interchangeably in the present disclosure, and indicate that the referred to element, component, structure, function, functionality, objective, advantage, operation, step, process, apparatus, system, device, result, or clarification, has the ability to be used, included, or produced, or otherwise stand for the proposition indicated in the statement for which the term is used (or referred to) for a particular embodiment(s).

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. An embolic protection device (EPD) configured for arrangement within a carotid artery, the EPD comprising:

a filament configured to include:

a first posterior device end and a second anterior device end;

an un-deployed state including at least a portion configured to fit within a lumen of a needle; and a deployed state wherein the filament automatically forms a linearly arranged helix comprising a plurality of turns wound in a first direction, the helix including:
a first support portion,
a second support portion, and
a filter portion comprising a plurality of closely spaced turns of the helix,
wherein:
the device is configured for deploying within a carotid artery of a subject in an implantation direction, such that the first posterior device end points towards a subject first end, and the second anterior device end points towards a subject second end,
the first direction of the helix corresponds to one of a clockwise or a counterclockwise direction upon the device being deployed in a carotid artery on a first side of a body of the subject,
the first direction of the helix corresponds to the other of the clockwise or counterclockwise direction upon the device being deployed in a carotid artery on a second side of the body of the subject, and
the filter portion:
is arranged between the first support portion and the second support portion linearly along an axis, and
the second support portion includes a diameter of between 0.1-2 mm less than a diameter of the first support portion.

2. The device of claim 1, wherein the first side comprises a left side of the body of the subject, and the second side comprises a right side of the body of the subject.

3. The device of claim 2, wherein the carotid artery on the left side of the body comprises a left carotid artery, and the carotid artery on the right side of the body comprises a right carotid artery.

4. The device of claim 1, wherein a distal end of the needle includes an opening and a bevel along a bevel plane.

5. The device of claim 1, wherein a distal end of the needle includes an opening and a bevel along a bevel plane.

6. The device of claim 1, wherein a bevel plane is arranged during implantation such that it faces a midline of the subject.

7. The device of claim 1, wherein a bevel plane is arranged during implantation such that it faces a lateral direction of the subject.

8. The device of claim 1, wherein a bevel plane is arranged during implantation such that it faces a caudal direction of the subject.

9. The device of claim 1, wherein a bevel plane is arranged during implantation such that it faces a cranial direction of the subject.

10. The device of claim 1, wherein a bevel plane is arranged during implantation such that it faces a midline of the subject and faces a caudal direction of the subject.

11. The device of claim 1, wherein a bevel plane is arranged during implantation such that it faces a midline of the subject and faces a cranial direction of the subject.

12. The device of claim 1, wherein a bevel plane is arranged during implantation such that it faces a lateral direction of the subject and faces a caudal direction of the subject.

13. The device of claim 1, wherein a bevel plane is arranged during implantation such that it faces a lateral direction of the subject and faces a cranial direction of the subject.

* * * * *